United States Patent [19]
Twisselmann

[11] Patent Number: 5,223,864
[45] Date of Patent: Jun. 29, 1993

[54] PHOROPTER

[75] Inventor: Lorenz Twisselmann, Prisdorf, Fed. Rep. of Germany

[73] Assignee: J. D. Möller Optische Werke GmbH, Wedel, Fed. Rep. of Germany

[21] Appl. No.: 538,644

[22] Filed: Jun. 14, 1990

[30] Foreign Application Priority Data

Sep. 6, 1989 [DE] Fed. Rep. of Germany ... 8910606[U]
Sep. 30, 1989 [DE] Fed. Rep. of Germany ... 8911690[U]
May 15, 1990 [DE] Fed. Rep. of Germany ... 9005493[U]

[51] Int. Cl.$^5$ .............................................. A61B 3/02
[52] U.S. Cl. .................... 351/233; 351/217; 351/216
[58] Field of Search ............... 351/205, 216, 217, 233, 351/235

[56] References Cited

U.S. PATENT DOCUMENTS 4,385,813  5/1983  Klein et al. .......................... 351/235
4,496,226  1/1985  Augusto et al. ..................... 351/235

Primary Examiner—Rodney B. Bovernick
Assistant Examiner—Hung Xuan Dang
Attorney, Agent, or Firm—Anderson Kill Olick & Oshinsky

[57] ABSTRACT

The phoropter is provided with a rotating knob means for selecting specific types of functions (12,13,14), the angular position being picked up by means of a pulse generator, e.g. a light barrier (8,9) in the form of an electric signal (amplifier 10) and, via a processing stage (11), more particularly a counter, is supplied to at least one function setting stage (12,13,14), while the requisite engagement of defined angular positions is effected with the aid of magnets (7), an angle indicating means for the cylindrical lens systems, whose angularity of the shaft position is indicated by light-emitting elements in order to facilitate the readability for the examining party, said light-emitting elements being arranged on the side of the examining party in a circular disposition around the viewing aperture and being operated in the bright state from a keyboard console in accordance with the shaft position, and a main support on a frame fitted with a forehead rest mounted on a phoropter housing protected against the environment by a covering, while, on the main support, two lateral supports are mounted so as to be approximately horizontally displaceable relative to each other, on which one shaft support each is attached with an approximately horizontal shaft about which the disks of a stack are rotatable, the parts mounted on the main support and on the left-hand and right-hand lateral supports each being protected by a partial covering and in which the partial covering of the main support is interconnected with the partial coverings of the lateral supports via a bellows each (FIG. 1).

33 Claims, 6 Drawing Sheets

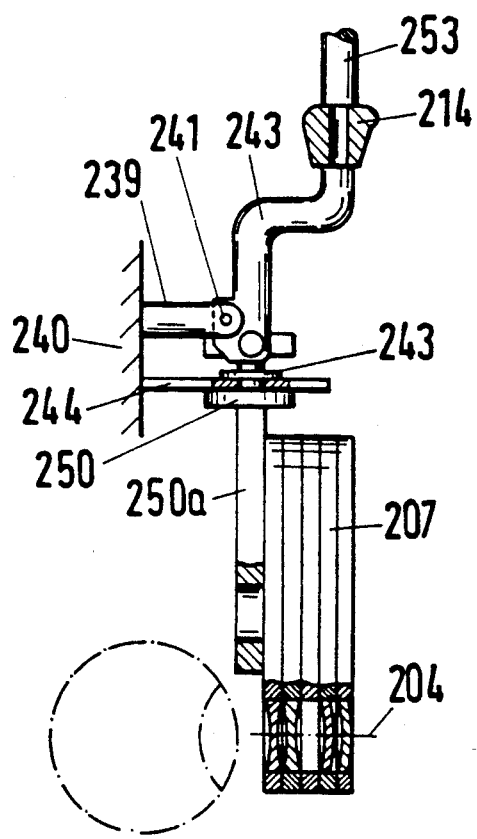
Fig.11
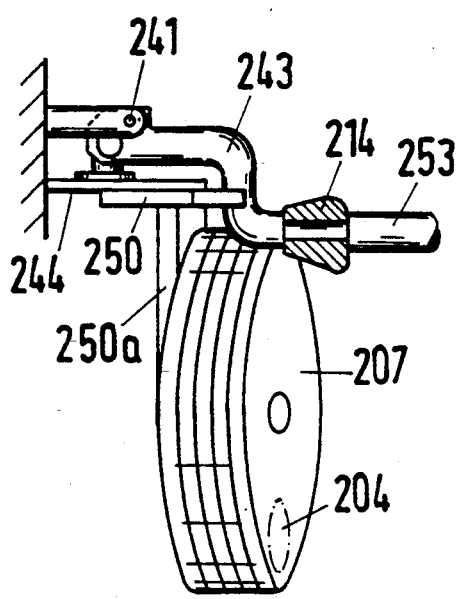
Fig.12
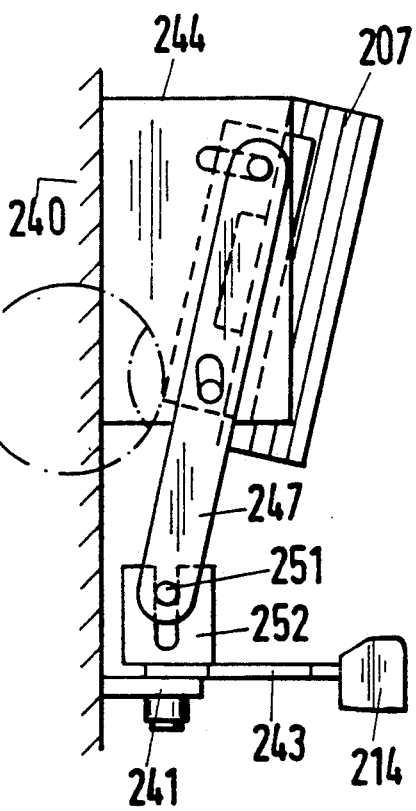
Fig.13
Fig.14

PHOROPTER

BACKGROUND OF THE INVENTION

The present invention relates to a phoropter for testing the visual acuity of a test person.

Phoropters are known in the most widely varying embodiments. Thus a phoropter is known with a rotating knob device for the selection of certain types of function of said device, in particular an electronic phoropter, by setting or adjusting a rotating part that is rotatable about an axis of rotation to certain positions defined by the angular position vis-à-vis a basic part.

These phoropters are actuated by turning mechanical switches into angular positions defined by mechanical engagement click stops. Such phoropters require a substantial amount of space and, particularly on account of the friction connected with the mechanical engagement, are difficult to operate.

Furthermore, a phoropter with several lens disks rotatably supported on at least one spindle in a frame and with a circular indicating means for the angular position of the shaft position of a cylinder component (cylinder shaft) of the optical system swung or swiveled into the light path, which is mounted so as to be rotatable about a setting spindle is known. In a phoropter known e.g. from the DE-PS 29 01 459, a plurality of lens disks is arranged in series, while on at least one disk, cylinder or crossed cylinder lenses may be disposed which each are rotatable about a setting spindle in order to be able in this way to change the angular position of the cylinder component. The angular position of the cylinder spindle lying transversely to the light beam axis or to the viewing direction can be read off from a scale graduation on the side facing the examining ophthalmologist. Due to the poor room illumination this causes considerable difficulties and may possibly lead to errors being committed. The indication and reading off may also be carried out on a keyboard console which is accordingly better illuminated and separated from the phoropter. This is inconvenient because the examining party is thus compelled to look in a different direction than that of the patient.

A further apparatus for testing the visual acuity of a test person (phoropter) is protected against the environment by a covering (housing). Furthermore, a forehead rest for positioning the head of the test person is attached to a frame and, for each eye, a stack holder or support, on which, rotatable about an approximately horizontal spindle, a stack of disks each is disposed which, in circular arrangement, carry a plurality of optical elements, more particularly, spherical and cylindrical lenses, of which one each of every disk is turned in front of a viewing aperture, the shaft of the one stack being, relative to the shaft of the other stack, adjusted vertically and, if necessary, swivelable for viewing a close-up reading test specimen. In apparatuses of this type, adjusting means are necessary on the disks of the optical elements, but also for the setting up of the stacks, said adjusting means being manually operated. For this purpose, the apparatus is provided with a number of openings through which, in the course of time, dust and other dirt particles penetrate which may particularly impair the surfaces of the lenses as well. When the housing covers all the component parts, it creates a shapeless and voluminous impression. When individual subassemblies are disposed so as to be separated from each other and actuating elements, e.g. rotating knobs, are mounted on the outside, an irregular impression is created and the mechanical linkages between the apparatus components likewise detrimentally affect the appearance and are prone to mechanical damage or to contamination.

It is the object of the invention to be able, in a phoropter, to effect the selection of the types of function without mechanical switches or the like that are directly connected to the device and to also simplify the click stop engagement by means of a minor structural expenditure. Moreover, it is the object of the invention to improve the indication of the angularity of a cylinder component of the phoropter and to facilitate, for the examining party, the obtaining of an immediate stereoscopic impression regarding the position of the shaft in relation to the eye to be examined. In addition, it is intended to construct a phoropter in such a compact manner that the parts to be moved will, if possible, all be covered and thus protected against extraneous effects and that, this notwithstanding, an overall tranquil and harmonious impression exists.

SUMMARY OF THE INVENTION

The technical problem of effecting the selection of the types of functions without switches or the like which are connected directly to the device and to also simplify the click stop engagement with an insignificant expenditure, is solved according to the invention in that the phoropter is provided with a rotating knob means for the selection of specific types of functions by setting a rotating part which is rotatable about an axis of rotation to specific positions defined by the angular position vis-à-vis a basic part, while, on the rotating part and on the basic part, a plurality of magnetic elements, of which at least one is fitted with permanently magnetic or electromagnetically excited magnetic poles, is disposed in a circular fashion about the axis of rotation which, during the rotation, are conducted closely past each other, and in that a pulse generator is coupled to the rotating part, which, during the rotation, by means of a pulse generator mounted on the basic part, supplies electric pulses for the further digital processing.

By means of the digital signals received, the switched stages can be arranged without difficulty so as to be spatially remote from the rotating knob means. Even a change-over is possible in order to effect a setting or adjustment of various types of functions in a selectable manner. It is thus possible e.g. in a phoropter, to change over alternately spherical lenses, cylindrical lenses or viewing fields with letters and figures of different types and sizes for the visual examination by a patient.

Since the formation of the electric pulses does not call for any appreciable mechanical forces, a stiff mechanical click stop engagement is not necessary either. The magnetic engagement employed permits a delicate adjustment without any application of force. The position assumed can be indicated by light signals that are discernible even in a blacked-out room, e.g. by the indication or display of the set dioptric number with the aid of light-emitting diodes.

Expediently, the supporting of the rotating part may be effected on ball races in order to ensure a smooth and easy movement also from this aspect.

According to an embodiment of the invention, a steel disk with rectangular toothing can be mounted on the rotating part and, on the basic part, closely opposite the toothing edge, at least one permanent magnet. The teeth of the steel disk are thus more or less attracted by the permanent magnet so that the desired engagement is produced. Expediently the permanent magnet is configured so as to be approximately U-shaped in such a way that a magnetic pole is located laterally near to the toothing and another pole opposite the front end of the toothing. A stronger magnetic flux and an accordingly more distinctly perceptible engagement is ensured. The angular position of the rotating knob can be scanned in that, on the one side of the toothing, a light source and, on the other side, a photoelectric transducer is disposed. By means of the teeth, the light beam is, from the source to the transducer, alternately released or suppressed so that, at the output of the transducer, pertinent pulse-like fluctuations take place. The toothing, the light source and/or the transducer may expediently be constructed in such a way that, with the movement of the toothing, an identifying signal regarding the direction of movement is supplied. It is thus possible, for instance, that the oppositely located flanks of a tooth possess a different inclination, which results in accordingly differently inclined pulse slopes. Said pulse slopes can be evaluated prior to the further digital processing.

According to another embodiment, a disk may be provided with magnetic poles; these are able, by means of magnetic sensors, e.g. coils disposed opposite this rim, to convert the change in the magnetic field into electric signals, or to be scanned by Hall effect elements, which themselves allow the strength of the magnetic field to be determined.

For the further digital processing, the pulses may be supplied to a pulse counter which adds them appropriately and, at a certain maximal value, resets them once more. The count then, with a suitable definition of the initial value, reproduces the angular position of the rotating knob means. This count may be supplied to a function setting or adjusting stage for setting the desired specific type of function. Between the pulse counter and the function setting stage, a change-over switch may be disposed, by means of which the count is transferred to a function setting stage which is manually selectable. It is thus possible to effect various adjustments or settings with the same rotating knob means, it being only necessary to effect a manual selection. Expediently, at the input of the function setting stage or at the output of the change-over switch, a memory is installed for every setting so that the setting for the function in question is maintained even if the change-over switch is moved into another position.

According to another further development of the invention, the spindle of the rotating part is displaceably supported over a certain section and connected to an electric switch in such a way that, by pressing or pushing, respectively, of the head portion, the switching-on operation is triggered.

The further technical problem, i.e. to improve the indication of the angular position of a cylinder component and to facilitate for the examining party the obtaining of an immediate stereoscopic impression of the position of the axis in relation to the eye to be examined, is solved in that the angular position is indicated or displayed by means of at least one of several light-emitting elements, e.g. light-emitting diodes (LED's) which are mounted on the side of the examining party on the frame in a circle around the viewing aperture.

The power of the lens swiveled in front of the eye and the angular position of the shaft of the optical system, e.g. a cylindrical lens, can be conveyed by means of position signals to an operating facility, preferably a computer and be displayed there and possibly printed out. The angular position has to be displayed with the accuracy or gradation according to the concept of the invention additionally or exclusively on the side of the examining party adjacent to the viewing aperture. In this case, one light-emitting element each may be operated in the bright state; it is expedient to operate in the bright state two oppositely located diodes on both sides of the viewing aperture, so that the position of the shaft is immediately discernible in a stereoscopic manner without any further reference element, e.g. the construction of the circular viewing aperture.

When using adjustable test lenses comprising a spherical and a cylindrical portion, the optical values of the spherical and of the cylindrical portion and the angularity of the spindle position are expediently supplied to a computer, in which the spindle position of the resulting crossed cylindrical optical component is computed and supplied to the light-emitting elements for display. Said angularity, which is only obtained by computation in the operating facility, can then be concretely depicted within the vicinity of the eye or of the optical elements of the phoropter disposed in front of the eye.

The angular position of two or more optical systems mounted in series in the path of the light beam with cylinder component can be displayed by light-emitting elements that are disposed in two or more concentric circles. In this way, too, the examining party is able to discern directly at the viewing aperture how the cylinder shafts of the individual correction systems are set. The light-emitting elements forming part of different optical systems may in this case expediently possess differing configurations or be of different colors. As configuration, particularly dots or strokes or bars come into consideration, but also stars or small annular elements with a dark center may be employed. The concentric circles may have different diameters, but thay may also possess the same diameter in such a way that at all times a light-emitting element assigned to the one cylinder shaft alternates with a light-emitting element assigned to another cylinder shaft. The size of the light-emitting elements and the density of their arrangement is expediently selected according to how high the angular resolution of the display has to be. On principle it is possible to choose a lower angular resolution for this display and to display the angular position actually set or adjusted on the console in figures or else by angular degrees having a higher resolution.

The technical problem of additionally constructing the phoropter in such a compact fashion that the parts to be moved are possibly all covered and thus protected against extraneous influences, whereby a smooth and harmonious impression is obtained, is solved in that, on the frame, a main support is mounted, to which two lateral supports are secured so as to be approximately horizontally displaceable relative to each other, on which one spindle support each with an approximately horizontal spindle is provided, about which the disks of a stack can be rotated, while the parts mounted on the main support as well as on the left-hand and right-hand lateral supports are each protected by a partial covering and the partial covering of the main support is interconnected with the partial coverings of the lateral supports by means of one bellows each.

The main support is rigidly anchored by means of the frame to a table or directly to the floor; it thus bears the entire weight of the phoropter. The lateral supports are displaceable relative to each other for setting the interpupillary distance and carry apparatus parts assigned to the left or the right eye. On the shaft supports, the disks of a stack of disks with correction lenses, etc., are mounted by means of joints and/ or tracks so as to render a swiveling into a convergence position about the center of rotation of the eye possible in order to adjust the optical elements during the close-up reading test according to the then changed position of the visual axes. A correction of the vertical position of one eye with respect to the other eye is also easily possible in this manner.

The structural members mounted on the main support and the parts mounted on the lateral supports are, each by itself, protected against any environmental influences by a housing, in particular by shell sections fitted on the front and on the rear, in connection with which only few parts project from these partial coverings, especially of the optical elements swiveled into the viewing aperture and of the mounting means in the direction of the main support. The partial coverings are interconnected by means of bellows, of the kind known e.g. in cameras, so that a dust-proof sealing is maintained even when the housing portions around the lateral supports are displaced relative to each other with the housing portions around the main support for adjustment and operating purposes. By preference, the bellow are provided with folds extending obliquely at e.g. 135 to 45° vis-à-vis the perpendicular line in the direction of the nose, by means of which it is possible to execute both horizontal as well as vertical displacements of the parts relative to each other in a simple manner and while maintaining a harmonious impression.

Advantageously, within the area of the shaft supports, the requisite operating members, gears and the like are disposed at the front, thus turned away from the face of the person whose eyesight is to be tested, and this more toward the outside, thus remote from the eyes. It is achieved hereby that, within the facial area, the device possesses only a slight structural depth which is chiefly due to the optical elements being located behind each other and, when looking through the same, a narrowing of the visual field and a possible instrument myopia are avoided.

The cylindrical part of the optical elements inserted in front of the eye can be indicated in that, in an annular fashion around the viewing aperture, light-emitting elements, more particularly light-emitting diodes, are installed which light up dependent on the shaft position and can thus be readily discerned by the ophthalmologist even in the darkened room. It is also possible, of course, for a display and registration of the shaft position to be effected on an assigned control console.

Normally, an optical system for the prism compensation is provided as well. In known assemblies, the prisms that are adjustable by turning, were moved into the viewing position when such a compensation was not necessary. The area of the viewing aperture is then in each case extended by this system. According to an advantageous further development of the invention, an assembly for the prism compensation is mounted on the side facing away from the test person in such a way that, in the normal case, the prism wedges are disposed outside the viewing aperture and are swiveled in front of the assigned viewing aperture for the prism compensation. An extension of the length of path at the viewing aperture thus only takes place for those patients for whom a prism compensation is required. Expediently, the prism compensation assembly is normally swivelled below the front partial covering and, with a bottom portion, closes the partial covering in a dustproof manner. The rotation of the prism parts may in this case be effected in a manner known per se, e.g. electromotively, in particular by means of stepping motors which can be easily operated by remote control. In order to be also able to carry out a correction of the visual faculty within the close range, a close-up reading test specimen can be swiveled, at a pertinent distance, in front of the viewing aperture, the stacks then being rotated about a vertical shaft for the requisite convergence adjustment of the optical elements. According to the invention, the adjustment of the close-up reading test specimen and the swiveling of the lenses into the close-up reading position are coupled so that both adjustments are effected with one actuating touch. The adjustments may be carried out electromechanically, e.g. by means of electromotors and switches, or by means of mechanical coupling members. In so doing, care has to be taken that the swiveling takes place about the center of rotation of the eye, which is located approximately in the center of the eyeball. The figure description contains a detailed embodiment.

Expediently, on the side of the test person, a construction may be mounted on the forehead rest which anatomically fits to the root of the nose and which causes the test person to assume a carriage of the head which is centered relative to the viewing apertures.

The adjustment and control means disposed in the phoropter components can be actuated and indicated from a console which is connected via control or interconnection lines, preferably in a common cable, to the device parts, especially to the main support and which is provided with a display that may be attachable. On the front panel of the console, besides operating keys and, possibly, light-emitting display elements, such as light-emitting diodes, a multifunction knob may be fitted with the aid of which, by pressing and/or turning, all preferably motor-actuated adjustments to the device, in particular the switching further of functions, can be effected.

Advantageous constructions of the invention are characterized in the subclaims.

DETAILED DESCRIPTION OF THE DRAWINGS

Figure 8:
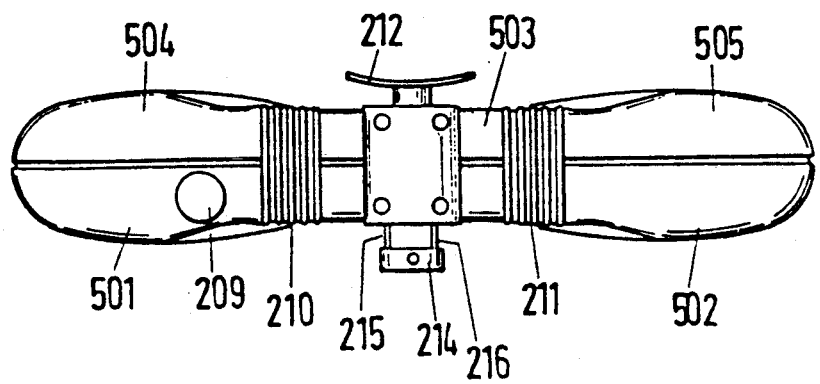
Figure 9:
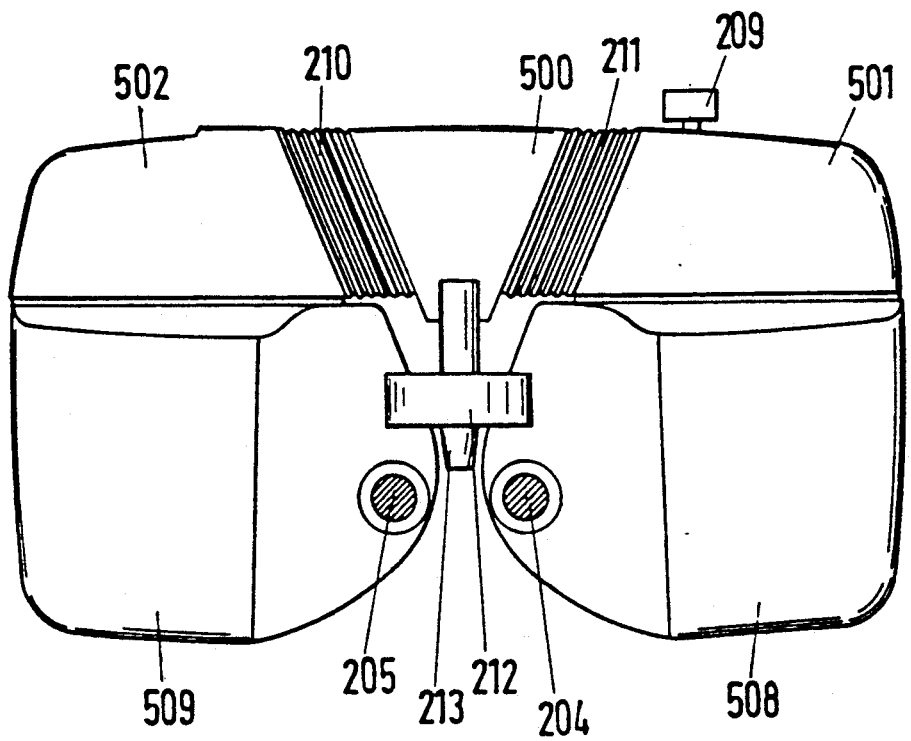

Embodiments of the invention are explained in the following in greater detail with the aid of the drawings. Thus FIG. 1, in a top view, shows a rotating knob means of the phoropter with its essential component parts, FIG. 2, in a side view, shows the rotating knob means, FIG. 3, in a view from below, shows the rotating knob means, FIG. 4, partly in a view and partly in a vertical section, shows the rotating knob means, FIG. 5, partly in a view and partly in a vertical section, shows a further embodiment of the rotating knob means with a switch tab provided on the underside, FIG. 6 shows a view onto a phoropter with an angle adjusting means, FIG. 7, in a front view, shows a phoropter with a main support and with two lateral supports that are displaceable relative to each other and mounted on said main support, carrying device components which are assigned to the right and to the left eye, FIG. 8 shows the phoropter in a view from the top, FIG. 9 shows the phoropter in a view from the rear, FIG. 10, in a diagrammatical view, shows a keyboard console with an attached display means, FIG. 11, partly in a side view and partly in a vertical section, shows an assembly in which, for a close-up reading test, the disk stacks can be swiveled into a convergence position about the center point of the eye, FIG. 12, partly in a side view and partly in a diagrammatical view, shows the disk stack assembly according to FIG. 11, FIG. 13, in a view from the top, shows the assembly according to FIG. 11 in the normal position, and FIG. 14, in a view from the top, shows the assembly according to FIG. 12 in the swiveled position.

DETAILED DESCRIPTION OF THE PREFERRED EMBODIMENT

Figure 1:
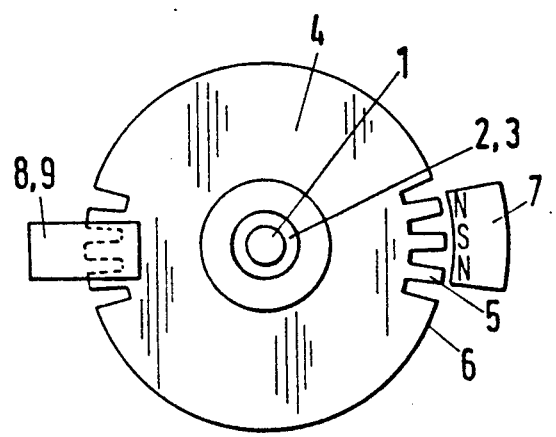
Figure 2:
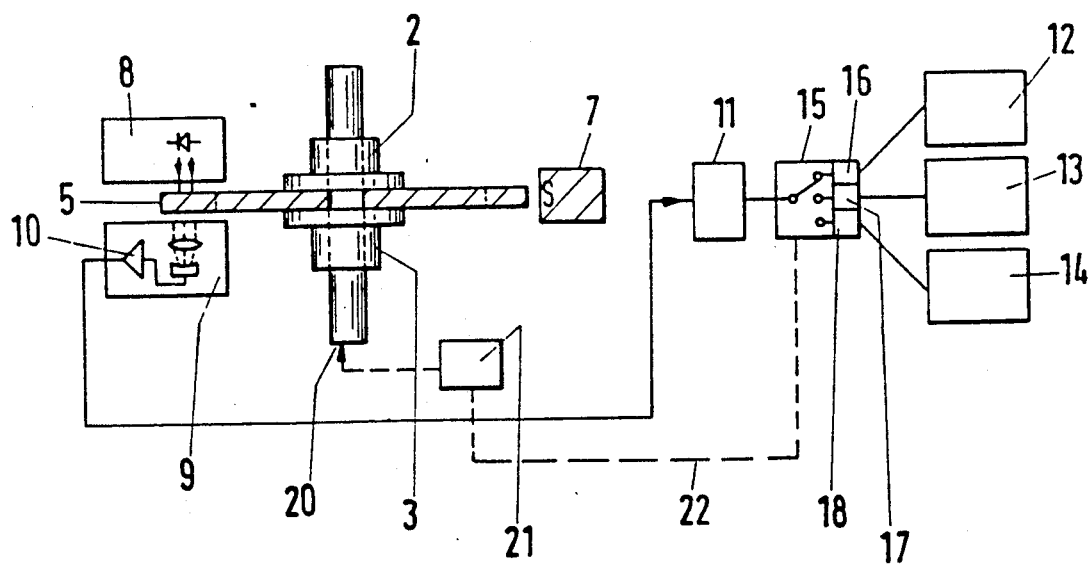

In the FIGS. 1 and 2, in a phoropter that is not shown in the drawing, a rotating knob spindle 1 is reproduced, on which, with the aid of flange-like means 2 and 3, a steel disk 4 is mounted which, on its rim, is provided with a rectangular toothing 5. FIG. 1 shows said steel disk 4 in a view from below, the teeth being indicated individually solely on the left-hand and on the right-hand side. On the right-hand side, on the circumferential line 6, a permanent magnet 7 is depicted which is provided on its sides with two magnetic north poles N and with a magnetic south pole S. On the left-hand side, located opposite the permanent magnet 7, a light barrier assembly 8,9 is mounted which is comprised of a light source part 8 and a photoelectric transducer part 9. The light source part 8 emits a thin beam of light in the direction of the transducer part 9 which, depending on the position of the toothing 5, is interrupted by a tooth or is allowed to pass through an interstice between two teeth.

FIG. 2 shows the assembly from a lateral direction of view, the steel disk 4 with the toothing 5 being sectioned, while the spindle 1 and the supporting flange-like members 2 and 3 are reproduced in a side view. The magnet 7 is also depicted sectioned.

The light received in the photoelectric transducer part passing through the interstices of the teeth is, via an amplifier, supplied to a signal processing stage 11 in which in particular a counter is comprised. When the spindle 1 and thus the disk 4 with the toothing 5 is rotated, pulse-like signals are transmitted which turn counter further. The assembly may be constructed in such a way that a rotation is only possible in one specific direction. In the counter 11, the arriving pulses are then added up to a value which corresponds to the total number of the teeth which represents the initial position for the rotation. In a further rotation, the counter is reset to the initial value. The count obtained thus has a clear allocation or assignment to the angular position of the shaft 1. This count is finally supplied to a function stage 12 and there determines a type of function, e.g. the adjustment to a specific lens power in a phoropter.

It is also possible to trigger or drive further functions setting stages 13 and 14 when, between the output of the processing stage 11 and the inputs of the function setting stages 12,13,14, a change-over switch is inserted. This switch can be actuated manually. Thus, with the same adjusting means, from the spindle 1, it is possible to select various function setting stages, e.g. with spherical lenses, cylindrical lenses or with different viewing fields with letters and/or figures of different sizes.

When a setting of the toothing 5 is to be admissible in both directions of rotation, it is necessary to pick up a further coded signal in a known manner and for it to be supplied to the counter 11, which indicates the direction of rotation.

In addition, at the output of the change-over switch 15 or at the outputs of the function setting stages 12,13 and 14, a memory means 16,17 or 18 each is mounted which records the count transmitted in the activated state from the counter 11 so that, even when the change-over switch is turned further, the function setting stage in question retains its assumed position.

When the spindle 1 is displaceable in the axial direction, then e.g. by means of an electric contact indicated with 20, a criterion regarding the position of the shaft of a setting stage 21 can be supplied. This may control any additional function whatever, e.g. switch the room lighting on or off. But its output signal may also control the change-over switch 15 by means of an operative connection in such a way that, at every pressure exerted upon the spindle 1 or the rotating knob connected with the same, a switching further of the change-over switch 15 takes place and the function setting stages 12,13 and 14 can in this way be successively brought into connection with the counter 11.

Figure 3:
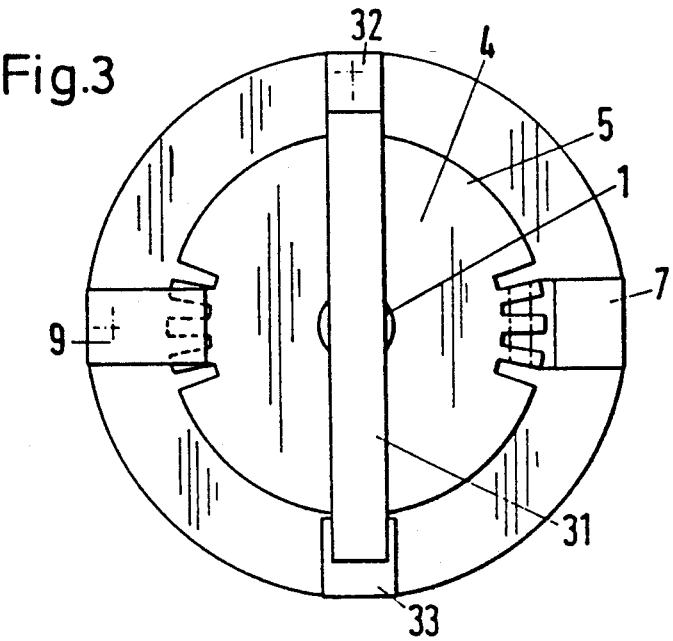
Figure 4:
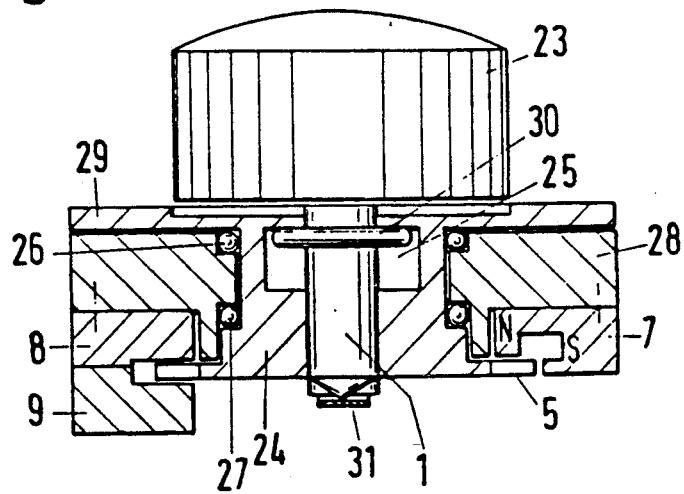
Figure 5:
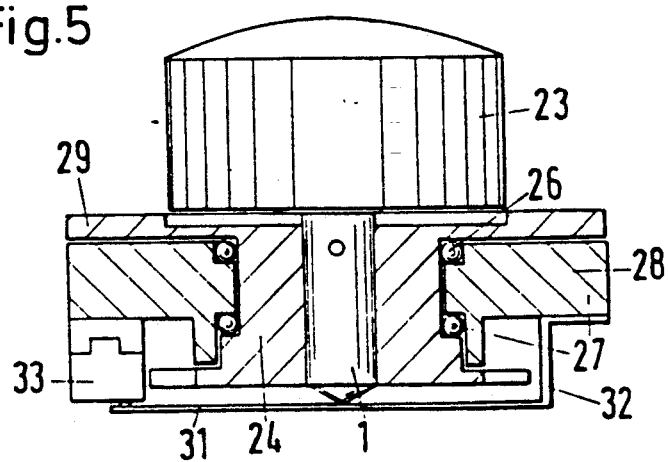
Figure 6:
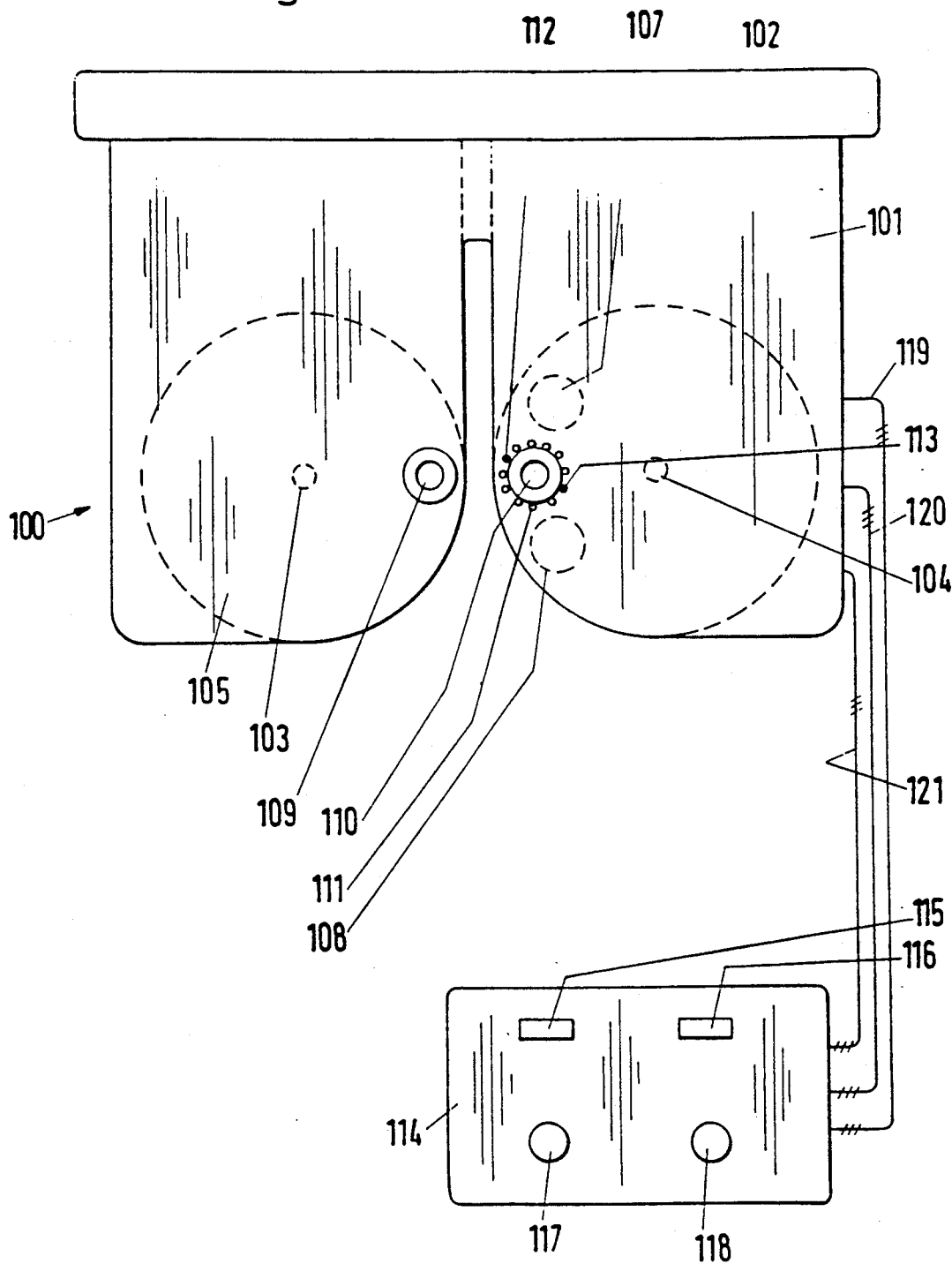

The FIGS. 3,4 and 5 provide a more detailed depiction of an embodiment example. In this case the spindle 1 carries a rotating knob 23 on its upper portion. The spindle 1 which, at its upper end, is rigidly connected to the rotating knob 23 is, at the bottom, displaceably mounted in a supporting part 24.

The support, in its turn, by means of ball bearings 26 and 27, is supported in a fastening fitting 28 which, on its part, can be secured to a keyboard console in a manner not shown. The supporting part, at its bottom, is rigidly connected to the steel disk 4 and, at the top, with an indicating disk 29. In the interior of the supporting part 24, a slot 25 is constructed in which an entrainment pin is disposed which passes through the spindle 1. The entrainment pin can be displaced inside the slot so that the rotating knob 23 can be moved upwardly and downwardly. In this case, the entrainment pin 30 in the slot brings about a positive connection in regard to the rotation. The position of the rotating part and, with it, of the steel disk 4, can be read off a marking on the indicating disk 25.

A leaf spring 31 is fitted to the lowerend of the knob, which, in the position according to FIG. 5, is fixed to the right-hand side of the attachment part 28, preferably electrically insulated, and which is able to actuate a microswitch 33 with its left-hand end.

FIG. 4 also depicts diagrammatically the light source part 8 and the transducer part 9 and, located opposite thereof, the permanent magnet 7 is shown which here is constructed in an approximately U-shaped manner and which engages around the toothing 5. In this case, the one pole, e.g. the north pole N, is able to act laterally on the teeth, while the magnetic south pole S acts upon the front end of the teeth. Thus a strong magnetic flux is achieved by means of the teeth; in this way the sensation of a distictly perceivable engagement comes about without, however, that frictional forces occur and have to be overcome in the rotation.

A rotational knob according to this type may be disposed in a keyboard for the control of electronic function setting stages, it being thus possible, by depressing a key, to set the knob into the desired function setting stage and, by rotating the knob, to obtain a desired function value. The values set can in this case be indicated by scales or by light signals.

The electric switch 33 may moreover likewise be constructed in the form of a light barrier, in which case the spring 31 dips between the light source and the photoelectric transducer and, when the spindle 1 is displaced, a switching operation can be initiated.

FIG. 6 depicts a phoropter, in which, in a frame 100 provided with a front plate 101 with a cross member 102 on shafts 103 and 104, disk-like lens supports 105 and 106 are disposed which, behind the frame 100 forming a front plate 101 are arranged so as to be rotatable.

On the lens supports 105 and 106, ten lens systems each are mounted in a circular fashion, of which, on the disk 106, the lens systems 108 and 109 are indicated in dashed lines. Behind the viewing apertures 109 and 110 shown with an annular edging, lens systems are likewise depicted.

Adjacent to the edging of the viewing aperture 110, twelve approximately dot-shaped light-emitting elements 11 are depicted in the form of small circles. When the cylinder shaft of the associated optical element (corresponding to 107 or 108) is rotated behind the viewing aperture 110 through e.g. 36°, those light-emitting elements can be excited which, in FIG. 6, are rendered by black dots 112 and 113 in lieu of the small circles. The examining party, who, in the FIG. 6, looks onto the plane of the drawing as it were, is thus able to immediately detect the pertinent shaft position and thus draw his or her conclusions regarding an optical correction requirement of the eye of the patient.

In this way the ability of the examining party to turn toward the patient is assisted and facilitated, moreover, the definite allocation of the display or indication in the actual angular position relative to the examined eye, be it the right or the left one, is ensured. Altogether, on the one hand, a faster and facilitated judgement of the state of the eye results and, on the other, a lower error frequency.

The lens disks on the whole and the individual optical systems with their cylinder shafts can be adjusted on a manner known per se by means of electromotors or the like. The adjustment or setting signals necessary for this can be supplied e.g. via a multicore interconnection line 121, from the keyboard console 114 to the motors not shown in the drawing and mounted in the frame 100.

Figure 7:
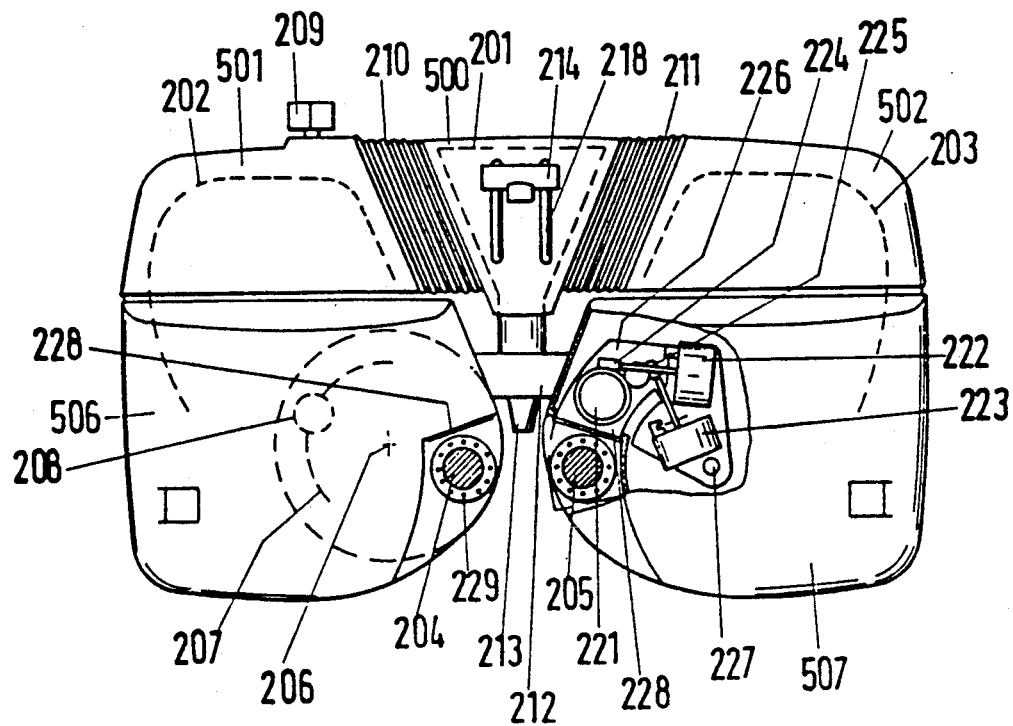

FIG. 7 shows a phoropter for testing the visual acuity of a test person seen from the doctor's point of view, in which connection the interconnected structural parts are disposed in a manner not shown in greater detail on a main support 201 and on lateral supports 202 and 203, the supports being protected underneath the partial coverings 500,501 and 502. The main support is, in a manner known per se and not shown in greater detail, connected to a frame, which e.g. is secured to a table and thus carries the entire device.

In the lower half, allocated to the lateral support 202 shown on the left and to the lateral support 203 shown on the right, the viewing apertures 204 and 205 are depicted, in front of which, from disks 207 rotatable about a shaft 206, optical elements, more particularly spherical and cylindrical lenses, can be swiveled. Moreover, in each case, several disks combined into a stack are located in a side-by-side arrangement which carry a plurality of such optical elements circularly disposed, as is indicated in dashed lines on the left-hand side of the FIG. 7. A corresponding assembly is also disposed in front of the viewing aperture 205 for the left eye. The shaft support for the shaft 206 can be adjusted by means of an actuating knob 209 in the vertical direction in order to compensate a possibly varying eye level of the test person. The lateral supports 202 and 203 are, in a corresponding manner, reciprocally displaceable for adjusting the viewing apertures 204 and 205 to the interpupillary distance. The partial coverings 500,501 or 502 are interconnected by means of bellows which provide a dustproof sealing and this even when these parts are displaced relative to each other.

FIG. 8 shows a view from the top of the phoropter according to FIG. 7. In this case it can be seen that the front coverings 501,502 and 503 are, on the rear side facing the test person, supplemented and terminated by partial coverings 504, 505 or 506 constructed in an approximately shell-shaped fashion.

On the side facing the test person, a forehead rest 212 is discernible in a manner known per se, which, as is shown by FIG. 7, according to an embodiment of the invention, is extended downwardly by a portion 213 which, by means of a suitable configuration, brings about that the nose, and with it, the entire face of the test person, rests, as far as this is possible, exactly in the center of the device.

Toward the front, a gripping piece 214 projects from the partial covering 500 in front of the main support 201, said gripping piece 214 being secured to two levers 215 and 216, which, when the gripping piece 214 is pushed downwardly, run in slots 217 and 218 of the partial covering 500. The disks with the optical elements indicated with 207 lie underneath partial coverings 506 or 507. Underneath these partial coverings, an assembly each for the prism compensation is mounted which consist of a prism compensator 221 formed of two optical elements which, by means of electromotors 222 or 223 and with the aid of worm gears 224 or 225, are able to adjust the optical elements in order to effect the prism compensation in the desired intensity and at the desired angle. The entire assembly for the prism compensation is secured to a plate 226 which can be swiveled about a shaft 227 in such a way that the prism compensator 221 is moved in front of the viewing aperture 205. When a prism compensation is not required, the plate 226 is swiveled back into the position shown in the drawing in such a way that the light path through the viewing aperture then remains unaffected. The plate 226 which, with its components, in the rest position, lies completely underneath the partial covering 507, is further provided with a bottom portion which, in the inwardly swiveled state, seals the aperture necessary for the outward swiveling so as to render it dustproof. A corresponding assembly is also disposed underneath the covering 506 in front of the right eye. The prism compensators are swiveled out manually, or, in a manner not depicted in greater detail, by means of electromotors actuated from a keyboard console.

For the compensation of vision defects, by means of the optical elements 208, also such elements are moved into the viewing aperture 204 or 205 which are not spherically, but cylindrically effective in a corrective manner. In order to provide an immediate impression for the ophthalmologist, the position of the cylindrical shaft, at any rate in certain stages, is indicated with the aid of light-emitting elements, more particularly light-emitting diodes 229, which are arranged in a circle around the viewing apertures 204 or 205, and of which in each case one or two oppositely located light-emitting diodes are operated in the bright state for indicating the axial direction.

FIG. 9 shows a phoropter according to FIG. 7 as seen from the side of the test person, with the forehead rest 212 and the nose rest indicated with 213 which is not described in greater detail.

Figure 10:
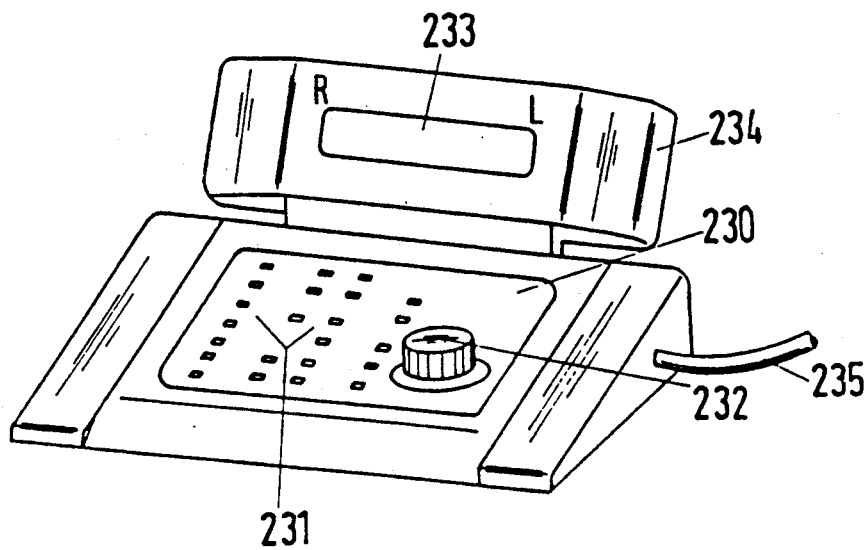

FIG. 10 shows a keyboard console 230 provided with control knobs and/or indicating lamps 231 and with a multifunction knob 232, by means of which, by rotating and/or pressing, it is possible in the phoropter to effect different functions for the actuation of individual structural elements and/or electromotors in order to set the desired correction for testing the visual acuity of a test person.

On the rear edge of the keyboard console 230, in an inclined position, inside a housing 234, a display means 233 is mounted. This housing 234 and/or the keyboard console 230, may contain the requisite computer elements in order to, all depending on the changes carried out in the device in front of the eyes of the test person, to cause the assigned optical values, etc., to be displayed and depicted on the display means 233. The keyboard console 230 is, in a manner not shown in any detail, by means of a cable 235, connected to the function elements forming part of the device according to the FIGS. 7, 8 and 9.

In order to be able to perform a close-up reading test in as natural as possible conditions, on the one hand, a field with appropriate characters has to be disposed a short distance of e.g. 40 cm in front of the eyes, thus approximately above the plane of the drawing of FIG. 7 or behind the plane of the drawing of FIG. 9, and, on the other, the optical correction elements have to be swiveled about the point of rotation of the eyes so that the test person continues to look straight through the viewing aperture. For this purpose, the disk stacks 207 have to be swiveled, in which case a mechanical or electromechanical coupling is expediently effected with the forward swiveling of the close-up reading test specimen. Details of such a mechanism are depicted in the FIGS. 11 and 12 in the side view or, in FIGS. 13 and 14, in a top view, to be more precise, in each case on the left in the normal position and on the right in the swiveled position.

On a supporting member 240, a holder 241 is fitted for this purpose, at the end of which a fulcrum point 242 is formed by a bearing or support, about which a lever 243 can be swiveled through approximately 90°.

In addition, a sliding block 244 is attached to the supporting member 244, which, according to FIG. 13, possesses an approximately rectangualr flat shape which is attached to the supporting member 240 with its longitudinal portion. Said sliding block has a slot 245 extending approximately parallel to the wall 240 as well as a slot 246 extending in a roughly curved manner. Above the sliding block 244, a rectangular plate 247 glides, on which, with approximately rod-shaped mounting means 248 and 249, a counter-plate 250 is mounted below the sliding block, on which a stack of disks 250 is mounted below the sliding block, on which a stack of disks 207 is disposed, with which optical elements are swiveled in front of the viewing aperture 204.

The plate 247 is depicted in FIG. 13 in the downward direction and, on its end, bears a pin 251 which is upwardly directed. When the lever 243, e.g. by means of a bar 253, is swivelled through 90° into the position shown in FIG. 12, the entrainment means 252 moves in the direction of the wall 240 into the position shown in FIG. 14. By means of this, the package of disks 207 is swiveled in such a way that the viewing aperture 204 is swiveled about the center of rotation of the eye indicated with 254 (FIG. 13).

On the bar 253, a coupling piece 214 is indicated, by means of which the allocated levers 243 (215 and 216 in FIG. 8) are interconnected in order to be able to perform a simultaneous and uniform swiveling in front of both eyes.

According to a further embodiment of the invention, the phoropter comprises a rotating knob means for selecting specific kinds of functions 12,13,14, in which case the angular position is received b y a pulse generator, e.g. a light barrier 8,9 in the form of an electric signal (amplifier 10) and, by means of a processing stage 11, more particularly a counter, is supplied to at least one function setting stage 12,13,14, while the necessary engagement of defined angular positions is effected with the aid of magnets 7, an angle indicating means for the cylindrical lens systems 107,108,110, whose angularity of the shaft position for facilitating the readability for the examining party is indicated by means of light-emitting elements 11 which are mounted on the side of the examining party around the viewing aperture and are operated from a keyboard console 14 in the bright state depending on the shaft position, and a construction, according to which the phoropter is protected against ambient influences by a covering (housing), and in which, on the frame, a forehead rest 212 is fitted for positioning the head of the test person and, for each eye, a stack support 207, on which, rotatatable about an approximately horizontal shaft 206, a stack of disks each is disposed which carry, in a circular arrangement, a plurality of optical elements 208, more particularly spherical and cylindrical lenses, of which one each of each disk is rotated in front of a viewing aperture 204,205, in which case the shaft of one of the stacks relative to the shaft of the other stack, can be vertically adjusted and, if necessary, be swiveled for viewing a close-up reading test specimen, an improvement of the impression received by the patient, in particular by means of a less daunting housing construction is achieved when, according to the invention, a main support 201 is fitted to the frame, on which two lateral supports 202,203 are mounted so as to be approximately horizontally displaceable relative to each other, on which one shaft support each is mounted with an approximately horizontal shaft 206, about which the disks 207 of a stack of disks are rotatable, while the members mounted on the main support 201 and on the left-hand and right-hand lateral supports 202, 203 are each protected by a partial covering 500,501,502, and in which the partial covering 501,502 of the lateral supports 202,203 is connected by means of a bellows 210 or 211 each. All these features are accommodated inside the housing of a phoropter, in which case also the rotating knob means, the angle indicating means and the means for the adjustment in the form of separate structural units can be disposed in individual phoropters.

What is claimed is:

1. A phoropter comprising a rotatable knob means for selecting specific functions, the rotatable knob means comprising a rotating part including a spindle rotatable about an axis of rotation, and a basic part, the rotating part being rotatable between predetermined positions defining angular position relative to the basic part, the rotating part and the basic part each having a plurality of magnetic elements circularly disposed around the rotating spindle, at least one of the magnetic elements having permanently or electromagnetically excited magnetic poles, the magnetic elements being mounted on the rotating part and the basic part such that they pass closely past each other when the rotating part is rotated, and a pulse generator coupled to the rotating part for supplying electric pulses for further digital processing by means of a pulse pick-up means mounted on the basic part.

2. The phoropter according to claim 1, further comprising a plurality of lens disks mounted on at least one shaft which is rotatably supported in a frame, the phoropter having an examination side, and a plurality of light-emitting elements arranged on the examination side on the frame in a circle around a viewing aperture, at least one of the light-emitting elements indicating in the angular positions.

3. The phoropter according to claim 2, wherein the light-emitting elements are light-emitting diodes.

4. The phoropter according to claim 1, wherein the rotating part is supported on ball races.

5. The phoropter according to claim 1, wherein a steel disk with rectangular toothing is mounted on the rotating part and at least one permanent magnet is mounted on the basic part closely opposite an edge of the toothing.

6. The phoropter according to claim 5, wherein the permanent magnet is U-shaped with two magnetic poles, one of the magnetic poles being located laterally adjacent the tooting and the other of the poles being located opposite a front end of the toothing.

7. The phoropter according to claim 6, comprising a photoelectric transducer disposed diametrically opposite the permanent magnet.

8. The phoropter according to claim 7, wherein the toothing, a light source and the transducer are constructed such that a movement of the toothing supplies an identifying signal regarding the direction of movement.

9. The phoropter according to claim 8, wherein the shaft of the rotating part is mounted so as to be displaceable over a certain distance and connected to an electric switch, the rotating knob moves having a head portion, whereby a switching operation is initiated by pressing the head portion.

10. The phoropter according to claim 9, wherein the electric switch is a light barrier for causing a spring to dip between the light source and the photoelectric transducer, and means for displacing the spindle for initiating a switching operation.

11. The phoropter according to claim 1, wherein the rotating part comprises a disk with a rim, magnetic poles being mounted on the rim in accordance with desired engagement positions, and magnetic sensors disposed opposite the rim for scanning the poles.

12. The phoropter according to claim 11, comprising means for supplying pulses to a pulse counter for further digital processing, and means for supplying a pulse count to a function setting stage for setting a specific type of function.

13. The phoropter according to claim 12, comprising a memory installed at an input of the function setting stage.

14. The phoropter according to claim 1, comprising adjustable testing glasses having a spherical part and a cylindrical part, means for supplying optical values of the spherical and cylindrical parts and the angularly of the shaft position in the form of electric signals to a computer, and means for supplying the shaft position of a resulting crossed cylindrical component for display to the light-emitting elements.

15. The phoropter according to claim 1, wherein the light-emitting elements are mounted substantially opposite each other relative to the center of the viewing aperture for displaying the angular position.

16. The phoropter according to claim 1, wherein the light-emitting elements are arranged in two or more concentrical circles for displaying the angular positions of the shafts of two or more optical systems with cylinder components being disposed in series in a light beam path.

17. The phoropter according to claim 16, comprising a plurality of colored light-emitting elements of different configurations.

18. A phoropter comprising:
a cover;
a frame covered by said cover,
a forehead rest which is secured to said frame for positioning a head of a patient on a patient side;
at least stack support for each eye wherein said at least one stack support is mounted in said frame;
at least one stack of disks wherein said at least one stack of disks is disposed on each of said at least one stack support, wherein each of at least one stack of disks is rotatable about an approximately horizontal shaft, and wherein each of said at least one stack of disks carries, in a circular arrangement, a plurality of optical elements, and further wherein one disk each is rotatable in front of a viewing aperture, wherein a shaft of one of said at least one stack of disks is vertically adjustable relative to said shaft of the other of said at least one stack of disks and is swivelable for viewing a close-up reading test specimen;
and wherein said phoropter further comprises:
a main support wherein said main support is mounted on said frame;
two lateral supports wherein said lateral supports are mounted on said main support, and wherein said two lateral supports are fitted so as to be approximately horizontally displaceable relative to each other;
a shaft support, each with one of said approximately horizontal shafts, is mounted on said lateral supports;
a plurality of partial coverings for protecting components which are mounted on said main support and for protecting components mounted on at least one of said lateral supports and on the other of said lateral supports; and
at least one bellows wherein said partial coverings of said main support are connected with said partial coverings of said lateral supports by means of said at least one bellows each.

19. The phoropter of claim 18, wherein said optical elements are at least one of spherical and cylindrical lenses.

20. The phoropter of claim 18, wherein at least one of said plurality of partial coverings comprises shell portions.

21. The phoropter of claim 18, wherein at least one of each of said at least one stack support and said at least one stack of disks, has associated therewith operating elements and gears disposed in a vicinity of the outside such that an area around said viewing aperture remains essentially unobstructed and has a small overall length.

22. The phoropter of claim 18, comprising:
a plurality of light-emitting elements annually arranged around said vexing aperture on a side opposite the patient side for displaying a shaft position of a cylindrical portion of optical elements inserted in front of the eye of the patient.

23. The phoropter of claim 22, wherein said light-emitting elements are light-emitting diodes.

24. The phoropter of claim 18, comprising:
an assembly for prism compensation which further comprises:
prism wedges wherein said prism wedges are mounted on a side opposite the patient side, so that, in a normal position of operation, said prism wedges are disposed outside said viewing aperture; and
a means for swiveling said prism wedges in front of an allocated viewing apertures for prism compensation.

25. The phoropter of claim 24, wherein said assembly for prism compensation is, in a normal position of operation, swiveled underneath an interior partial covering and seals, in a dustproof manner, said partial coverings with a bottom portion.

26. The phoropter of claim 18, comprising:
a mounting means for swiveling a close-up reading test specimen in front of said viewing aperture, wherein said mounting means is coupled to members for providing a convergence adjustment of viewing directions.

27. The phoropter of claim 26, comprising:
levers which are mounted on each of said lateral supports by means of a retaining member, wherein each of said levers is mounted so as to be swiveled about an approximately right angle, and further wherein each of said levers carries a fixed connecting link in the form of a horizontal disk with slots, and further wherein at least one of said slots is approximately straight and extends parallel to the forehead of the patient and the other of said slots has a shape of a circular arc portion and extends approximately perpendicularly to the forehead of the patient; and wherein said phoropter further comprises:
two downwardly extending members supporting bearings of an associated one of said at least one stack support and said at least one stack of disks, wherein said downwardly extending members are secured through said slots to a flat guide lever which is slidable on said connecting link and which, at an end extending toward the center, is displaceable approximately perpendicularly to a front plane, such that at least one of said at least one shaft supports and said at lest one stack of disks of the optical systems, which are normally in a parallel position, are inclined relative to each other in said viewing apertures for a close-up reading specimen.

28. The phoropter of claim 27, comprising electromotors for effecting horizontal swiveling of one of said at least one stack supports and said at least one stack of disks, wherein said electromotors are controlled by means of switches coupled to said close-up reading specimens.

29. The phoropter of claim 18, comprising:
a means mounted on an examination side for causing the patient to assume a head position which is centering relative to said viewing apertures.

30. The phoropter of claim 18, comprising:
a keyboard console for adjusting and control members, wherein said keyboard console is connected to said main support by means of a common cable, and wherein said keyboard console further comprises a display means.

31. The phoropter of claim 30, wherein said keyboard console further comprises:
a control panel with operating keys and indicator lights, wherein said control panel further comprises: a multi-functional knob for carrying out adjustments.

32. The phoropter of claim 18, comprising mounting means for swiveling a close-up reading test specimen in front of a viewing aperture.

33. A phoropter comprising:
a rotating know means for selecting specific functions;
a pulsing device for picking up an angular position of said rotating knob means in the form of an electric signal;
a processing stage for supplying said signal to at least one function setting stage;
a plurality of magnets for effecting engagement of defined angular positions;
an angle display means for a cylindrical lens system, wherein an angularity of a shaft position is displayed by means of light-emitting elements to an examination side, and further wherein said light-emitting elements are mounted on the examination side and are arranged in a circle surrounding a viewing aperture and are operated in a bright stage from an operating facility in accordance with said shaft positions, wherein said phoropter further comprises:
a cover for protecting said phoropter;
a forehead rest wherein said forehead rest is mounted on a frame for positioning the head of a patient;
a stack support which is provided for each eye;
a stack of disks which is disposed on each of said stack support so as to be rotatable about an approximately horizontal shaft, wherein each optical element is rotated by each of said stack of disks in front of a viewing aperture, and further wherein said shaft of one of said stack of disks is adjustable vertically relative to said shaft of the other of said stack of disks is swivelable for viewing a close-up reading test specimen, and wherein said phoropter further comprises:
a main support wherein said main support is mounted on a frame which two lateral supports are mounted so as to be approximately displaceable relative to each other for improving an impression gained by the patient;
a shaft support wherein each of said shaft supports is mounted on said lateral supports with approximately horizontal shafts, wherein said disks of each of said stack of disks are rotatable about said shafts;
a partial covering for protecting components parts which is mounted on a left-hand and a right-hand lateral support;
at least one bellows; and
a partial coverings for said main support which is interconnected with said partial coverings of said lateral supports by means of said at least one bellows each.

* * * * *